United States Patent [19]
Gross

[11] Patent Number: 4,784,647
[45] Date of Patent: Nov. 15, 1988

[54] CATHETER MEATAL PAD DEVICE
[75] Inventor: James R. Gross, St. Charles, Ill.
[73] Assignee: The Kendal Company, Boston, Mass.
[21] Appl. No.: 891,930
[22] Filed: Jul. 30, 1986
[51] Int. Cl.[4] .............................................. A61M 25/02
[52] U.S. Cl. .................... 604/178; 128/DIG. 26; 604/265
[58] Field of Search ............... 604/265, 266, 174, 178; 128/325, DIG. 25

[56] References Cited

U.S. PATENT DOCUMENTS

| | | | |
|---|---|---|---|
| 2,046,094 | 6/1936 | Schmidt | 128/DIG. 26 |
| 2,898,913 | 8/1959 | Ritter et al. | 128/325 X |
| 3,046,988 | 7/1962 | Moreau et al. | 128/325 |
| 3,487,837 | 1/1970 | Petersen | 128/DIG. 26 |
| 3,604,426 | 9/1971 | Erikson | 604/265 |
| 3,606,889 | 9/1971 | Arblaster | 604/171 |
| 4,069,826 | 1/1978 | Sessions et al. | 604/178 X |
| 4,419,097 | 12/1983 | Rowland | 604/180 X |

Primary Examiner—Dalton L. Truluck
Attorney, Agent, or Firm—Donald Halgren

[57] ABSTRACT

A meatal pad for use with a catheter applied to a urinary tract for drainage thereof. The pad comprises a cylindrically shaped block of foam material coated on on longitudinal end with covering of silicone, latex, or polyurethane. The pad and coating have a longitudinal bore therethrough, which has a slit radially directed therefrom, to facilitate mating of said pad with a catheter shaft. The pad may be treated with an anti-bacterial compound, and the uncoated pad is directed towards the meatus of the catheterized patient, thus minimizing bacterial growth thereat.

3 Claims, 1 Drawing Sheet

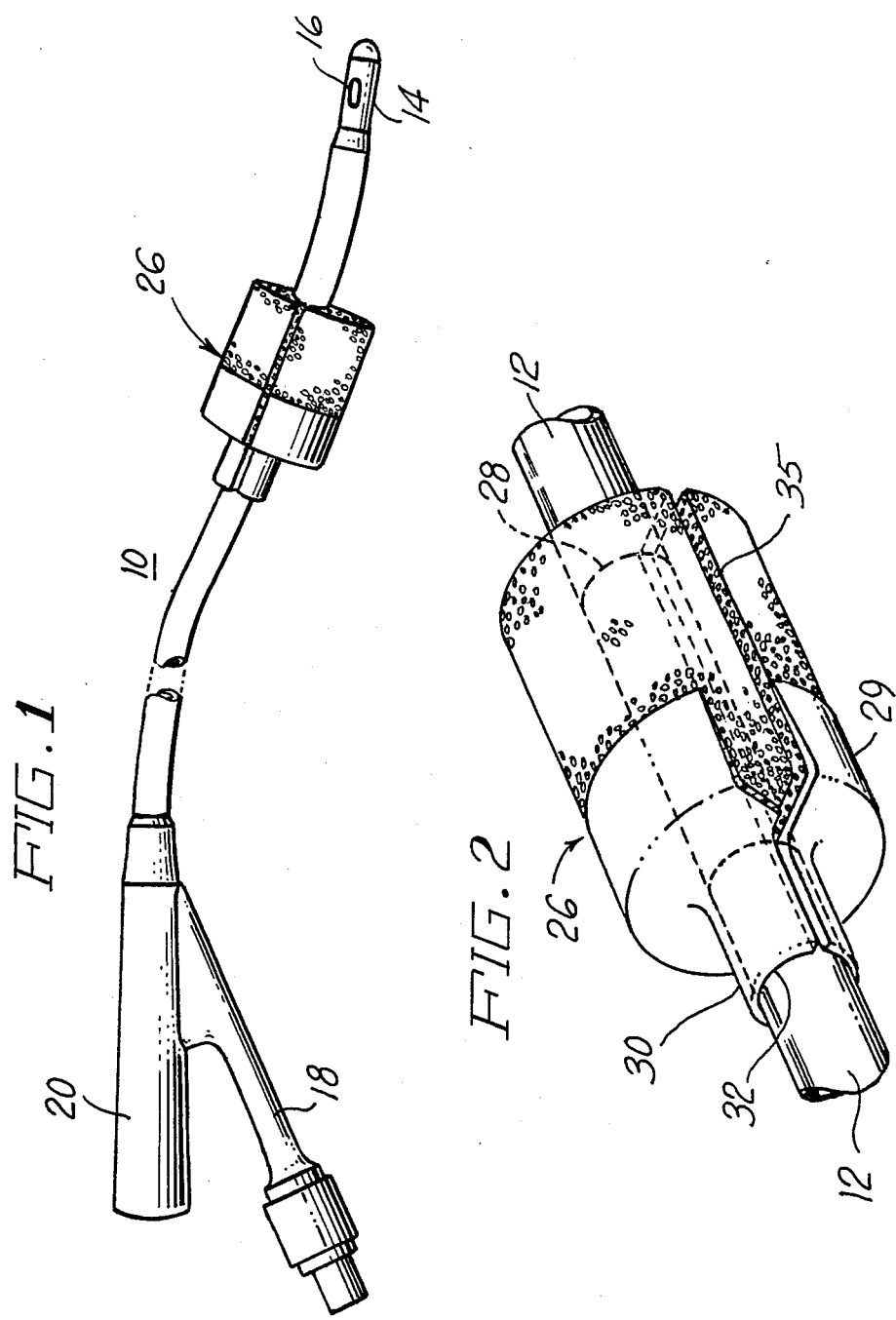

CATHETER MEATAL PAD DEVICE

BACKGROUND OF THE INVENTION (1) Field of the Invention

This invention relates to catheters and more particularly to catheter antibacteriological devices.

(2) PRIOR ART

Urinary catheterization has become common in the management of the hospitalized patient. It has however, serious risks. The urinary tract is the most common site of nosocomial infections. Urinary catheterization is a major cause of urinary tract infections. Half of the patients with catheterization bladders, found in one investigation, developed bacteriuria, within fourteen days thereof. A scruplous aseptic technique is mandatory when inserting a urinary catheter into a patient.

The most common catheterization route is via insertion of the catheter through the external meatus into the urethra, past the internal sphincter and into the bladder.

In one particular catheterization operation, such as a transurethral resection, which is useful for removal of the prostate, a three way Foley catheter is inserted into the bladder to provide hemostasis and to facilitate urinary drainage. An uninflated retention balloon is presurized in the resected area to compress the tissue therein, and to reduce bleeding. Traction has been accomplished by adding small weight to the exposed end of the catheter.

Obviously, attaching a weight to a catheter to maintain traction, is not the most desirable approach to take. One example of a catheter fixation device attached to a medicated pad is shown in U.S. Pat. No. 4,516,968 to Marshall et al. A ventilated dome is disposed about a catheter, and a gauze strip is placed between the dome and the patient's skin where the catheter enters therethrough. The dome is held restricted to the catheter by a tape strip. This approach can further complicate the infection of the catheterized patient.

A further tube clamp with a pad is shown in U.S. Pat. No. 4,069,826 to Sessions et al. wherein a spring biased lever is movably disposed in a housing about a tube. The tube has a distal end which is inserted into a patient and configured so as to enter a blood vessel therein. A sponge and o-ring are further provided about the distal end of the surgical tube adjacent the patient, to prevent leakage thereby.

Smith Industries PLC of London, England, makes a polyfoam collar for use with balloon catheters to act as a barrier against bladder infection. This collar which is merely an annular foam pad, must be slid onto the catheter from its distalmost end before the catheter is applied to a patient. The collar also has no anti-back off features to keep it snug against a patient.

It is an object of the present invention to provide a medicated pad means for a catheter in a patient which is simple, sterile and economical to manufacture.

It is a further object of the present invention to provide a medicated pad means for a catheter device for a patient, which is easily applied to the catheter and hence to the patient, is readily changeable, provides some resistance to slippage on the catheter, but yields on the catheter when the physical movement of the patient requires it.

BRIEF SUMMARY OF THE INVENTION

The present invention comprises a device for the prevention of urinary tract infection, by being positioned on the catheter against the meatus of the patient. The device is a meatal pad of generally cylindrical shape, made from a sponge material. The pad has an axial bore therethrough. The pad may have a shaft extended into the axial bore during manufacture thereof, so that the shaft may be utilized to hold the pad. One half of the pad is then coated with an outer skin of silicone, latex, polyurethane or the like.

The coating operation may be done by dipping the pad into a reservoir, or by a spraying thereon of the coating material.

The coating material may be applied to a portion of the holding shaft, so as to also provide a boss extending off of one end of the cylindrical pad. The boss has a central opening which is in coaxial alignment with the bore extending through the pad.

The pad and coating have a generally radially directed slit extending longitudinally therethrough. The slit permits the coated pad to be opened so that a catheter may snugly fit within the bore thus permitting application after the catheter is in the patient. The boss provides an amount of friction between the coating and the catheter to limit the spontaneous slidability therebetween. The pad may be treated with an anti-bacterial agent or medicament so as to reduce the bacterial count in the area of the patient so treated. After the catheter has been inserted into the uretera of the patient, the pad (with the medicated uncoated end directed towards the patient), is slid up so that the uncoated portion of the pad touches the meatus of the patient. This is the meatal catheter junction, which is a critical location where bacteria may otherwise enter a urinary drainage system.

BRIEF DESCRIPTION OF THE DRAWINGS

The objects and advantages of the present invention will become more apparent when viewed in conjunction with the following drawings, in which:

FIG. 1 is a view of the present invention disposed on a catheter; and

FIG. 2 is a perspective view of the present invention.

DESCRIPTION OF THE PREFERRED EMBODIMENT

Referring now to the drawings in details and particularly to FIG. 1, there is shown a catheter assembly 10, comprising a Foley catheter 12 having a tip 14 with a drainage eye 16 therein, a sidearm 18 and a connection portion 20.

A meatal pad 26 is shown disposed about the shaft of the catheter 12. The pad 26 is shown more clearly in FIG. 2. The pad 26 is generally cylindrically shaped, and may be made from a sponge-like foam block of material such as foam rubber or the like. The pad 26 has a centrally located axial bore 28 extending therethrough, of about the same diameter as the outer diameter of the catheter with which it is to mate.

In the manufacture of the pad 26, a shaft, not shown, may be disposed through the bore 28 so to hold the pad 26 during its subsequent treatment. About one longitudinal half of the pad 26 has a coating 29, comprised of a flexible, resilient rubbery layer of silicone, latex, polyurethane or the like. The coating of the pad 26 may be done by dipping the pad into a reservoir of coating material, or the coating may be sprayed thereon. The coating material is applied to a portion of the holding shaft, so that once the holding shaft is removed from the pad 26, a boss 30 is arranged to extend off of and is unitary with the coating 29 on the coated end of the pad 26. The boss 30 has an opening 32 therethrough, which is in coaxial alignment with the bore 28 through the pad 26.

The pad 26, including the coating 29 and boss 30, has a generally longitudinally directed slit 35 extending generally radially outwardly from the bore 28 and opening 32. The slit 35 permits the coated pad 26 to be opened so that the bore 28 and opening 32 may be split and then manually fit around a catheter shaft, as shown in FIG. 1, even after the catheter has been applied to a patient. The boss 30, comprising a supplemental extension of the bore 28, provides a friction fit between the coating 29 and any catheter around which the pad 26 is to mate. This friction fit acts as an anti-slip means to resist sliding down the catheter 12 away from the patient during normal minor body movement.

The pad 26 may be impregnated with an anti-bacterial agent or medicament such as povidone-iodine prior to or subsequent to the disposition of the pad 26 onto the catheter 12.

The uncoated portion of the pad 26 is pushed up the catheter and against the patient, once the catheter has been fully and properly inserted into the patient.

The treated meatal pad 26 minimizes the likelihood of bacterial migration into the urinary drainage system, once the catheter and pad 26 are in place.

I claim:

1. A metal pad for use in connection with a catheter, to minimize urinary tract infection associated with the meatus-catheter junction, and metal pad comprising:
   a foam block of material having a first and second end;
   a centrally located bore extending through said foam material;
   a flexible coating of material disposed about said first end of said foam block;
   a slit arranged radially outwardly from said bore through said foam block and said coating thereon, so as to enable said pad including said coating to be readily opened and disposed about a catheter shaft;
   said coating material annularly covering about one-half of said foam material;
   said coating material also unitarily comprising an anti-slip means comprising a boss which extends off of the coated end of said foam material;
   said foam block thus presenting a non-coated surface at the pad-meatus junction.

2. A metal pad for use in conjunction with a catheter, as recited in claim 1, wherein said foam block of material is of cylindrical shape.

3. A meatal pad for use in conjunction with a catheter, as recited in claim 1, wherein said coating material is selected from the group comprising silicone, latex or polyurethane.

* * * * *